United States Patent [19]

Johnson et al.

[11] Patent Number: 4,845,976
[45] Date of Patent: Jul. 11, 1989

[54] METHOD AND APPARATUS OF DETERMINING ENERGY CONTENT OF A DILUTED HYDROCARBON GAS

[75] Inventors: James E. Johnson; Raymond J. Magott; Clinton M. Wood, all of San Antonio, Tex.

[73] Assignee: Gas Researach Institute, Chicago, Ill.

[21] Appl. No.: 242,992

[22] Filed: Sep. 12, 1988

[51] Int. Cl.⁴ ............................................. G01N 25/48
[52] U.S. Cl. .......................................... 73/23; 374/36
[58] Field of Search ................... 73/23, 27 R; 374/36, 374/31; 324/71.1, 61 R, 65 R

[56] References Cited

U.S. PATENT DOCUMENTS 3,095,728  7/1963  Kindred et al. ................ 374/36 X
3,560,160  2/1971  Lamneau .
4,345,463  8/1982  Wilson et al. ...................... 374/36

Primary Examiner—Stewart J. Levy
Assistant Examiner—Joseph W. Roskos
Attorney, Agent, or Firm—Fulbright & Jaworski

[57] ABSTRACT

A method and apparatus of determining the energy content of a hydrocarbon gas mixture having a diluent gas. The dielectric constant of the hydrocarbon gas mixture and diluent gas is measured, the gas mixture is then directed through a separation column which extracts a mixture containing the diluent gas. The dielectric constant of the extracted mixture is then measured, and the energy content of the hydrocarbon gas mixture and dilute gas is calculated from the dielectric measurements. After use, the separator column and dielectric measuring cell are purged of the residual gases.

9 Claims, 3 Drawing Sheets

SPECIFIC GRAVITY - DIELECTRIC
PLANE OF SELECTED GASES

TABLE I

SPECIFIC GRAVITY AND DIELECTRIC
FOR FIVE PURE HYDROCARBON MIXTURES

| COMPOUND | VOLUME MOLE FRACTIONS | | | | |
|---|---|---|---|---|---|
| | No. 1 | No. 2 | No. 3 | No. 4 | No. 5 |
| METHANE | .95 | .925 | .90 | .875 | .85 |
| ETHANE | .02 | .03 | .04 | .05 | .06 |
| PROPANE | .000 | .005 | .01 | .015 | .02 |
| ISO-BUTANE | .01 | .01 | .01 | .01 | .01 |
| N-BUTANE | .01 | .01 | .01 | .01 | .01 |
| ISO-PENTANE | .01 | .01 | .01 | .01 | .01 |
| N-PENTANE | .00 | .01 | .01 | .01 | .01 |
| HEXANE | .00 | .00 | .01 | .01 | .01 |
| HEPTANE | .00 | .00 | .00 | .01 | .01 |
| OCTANE | .00 | .00 | .00 | .00 | .01 |
| SPECIFIC GRAVITY | .6120 | .6411 | .6750 | .7137 | .7573 |
| $\varepsilon - 1 \times 10^3$ | .8792 | .9139 | .9545 | 1.001 | 1.054 |

FIG. 3

TABLE II

SPECIFIC GRAVITY AND DIELECTRIC FOR
BINARY MIXTURES OF METHANE AND NITROGEN

| %$N_2$ | %$CH_4$ | $(\varepsilon-1) \times 10^{-3}$ | SG |
|---|---|---|---|
| 0 | 100 | .8093 | .5539 |
| 10 | 90 | .7827 | .5952 |
| 20 | 80 | .7560 | .6368 |
| 30 | 70 | .7294 | .6779 |
| 50 | 50 | .6761 | .7606 |
| 70 | 30 | .6229 | .8432 |
| 90 | 10 | .5696 | .9259 |
| 100 | 0 | .5430 | .9672 |

FIG. 4

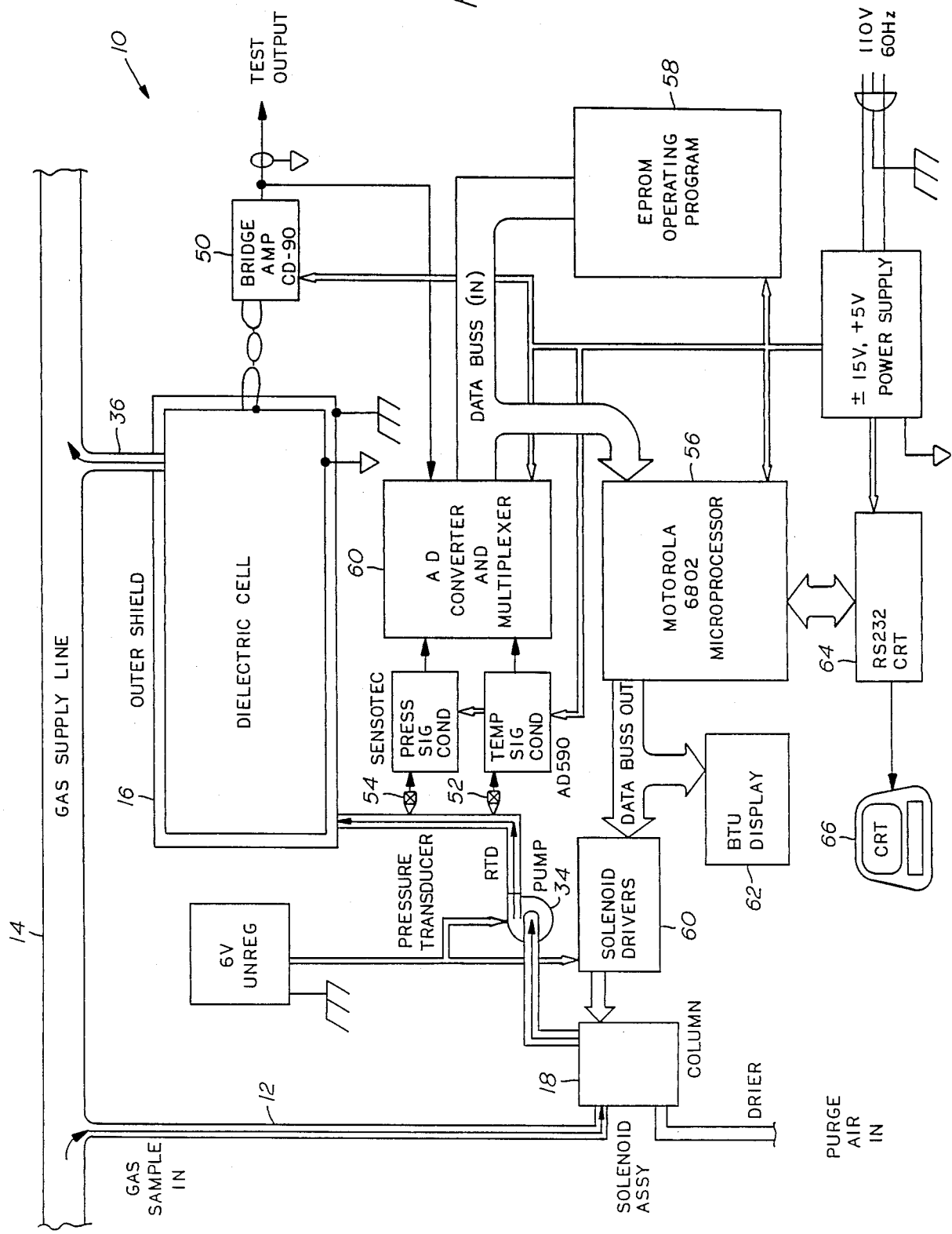

METHOD AND APPARATUS OF DETERMINING ENERGY CONTENT OF A DILUTED HYDROCARBON GAS

BACKGROUND OF THE INVENTION

The energy content (calorific value) of a hydrocarbon gas mixture such as fuel gases may widely vary. Purchasers of fuel gas are concerned about the energy content of the fuel and, in addition, industrial consumers need detailed information about gas components which affect their plant processes.

The energy content of a hydrocarbon mixture is directly related to the dielectric constant of the gas mixture. However, this well behaved relationship is altered when a non-hydrocarbon gas is present in the hydrocarbon gas mixture and dilutes the mixture.

The present invention is directed to the provision of a method and an apparatus which determines the energy content of hydrocarbon gas mixtures having one or more diluent gases present. The present invention is directed to a method and an apparatus for inferring the energy content of hydrocarbon gas mixtures such as natural gas. The present method and apparatus indirectly measures energy content based upon the relationship between the specific gravity of the gas and the gas dielectric along with the ability to compensate for one or more diluent gases such as nitrogen and carbon dioxide in natural gas.

SUMMARY

The present invention is directed to a method and apparatus for determining the energy content of a hydrocarbon gas mixture having a diluent gas by measuring the dielectric of the combination of the hydrocarbon gas mixture and diluent gas, and passing the combination through a separation column for extracting a mixture containing the diluent gas. Since the diluent mixture is approximately equal to its concentration in the combination mixture, the dielectric of the extracted mixture is measured thereby allowing the energy content of the energy hydrocarbon gas mixture and diluent gas to be determined from the dielectric measurements.

Still a further object of the present invention is wherein the dielectric is measured by a dielectric cell and the separation column and the dielectric cell are first purged prior to the measurements. Preferably the separation column and dielectric cell are first purged in series and thereafter the dielectric cell is separately purged.

Yet a still further object of the present invention is the method of determining the energy content of a hydrocarbon gas mixture having first and second diluent gases. The dielectric constant of the combination of gases is measured and the combination is passed through a separation column for extracting a first mixture containing the first diluent gas and thereafter a second mixture containing the first and second diluent gases. The dielectric constant of the first extracted mixture is measured and thereafter the dielectric constant of the second extracted mixture is measured. The energy content of the hydrocarbon mixture may then be calculated from the dielectric measurements.

Yet a still further object of the present invention is the provision of an apparatus for determining the energy content of a hydrocarbon gas mixture having a diluent gas which includes a hydrocarbon gas inlet line for receiving a hydrocarbon gas mixture and a dielectric measuring cell connected to the gas inlet line. A column separator having an inlet is connected to the gas inlet line and an outlet is connected to the dielectric measuring cell. A purge gas line is connected to the column separator and to the dielectric cell. Valve means are connected to the gas hydrocarbon inlet line, the separator, the measuring cell and the purge gas line for sequentially controlling the flow of a hydrocarbon gas mixture at the hydrocarbon gas inlet and the purge gas at the purged gas line for purging the separator and dielectric cell with purged gas, measuring the dielectric of the gas in the hydrocarbon gas inlet, and measuring the dielectric of the gas from the outlet of the column separator. Means are provided connected to the dielectric cell for receiving the dielectric measurements and calculating the energy content of the hydrocarbon gas mixture.

In addition, temperature and gas pressure measuring means may be connected to the dielectric cell for compensating the measurements for variations in temperature and pressure.

Yet a still further object of the present invention is wherein the dielectric cell is connected to a bridge amplifier and bridge circuit for greater sensitivity.

Still a further object of the present invention is wherein the column separator includes a packed column of activated charcoal for transforming the multicomponent mixtures in the gas into simple binary mixtures requiring only a simple low cost detection cell for quantification.

A further object is the provision of a dielectric measuring cell which includes a pair of coaxially positioned metal cylinders forming a capacitor.

Other and further objects, features and advantages will be apparent from the following description of a presently preferred embodiment of the invention, given for the purpose of disclosure, and taken in conjunction with the accompanying drawings.

BRIEF DESCRIPTION OF THE DRAWINGS

FIGS. 3 and 4 are tables used in evolving the measurement formulas of the present invention, and FIG. 5 is a block schematic of the present invention.

DESCRIPTION OF THE PREFERRED EMBODIMENT

While the description of the present invention will be described in connection with measuring the energy content of natural gas mixtures which include a diluent gas such as nitrogen and carbon dioxide, for purposes of illustration only, the present invention is also applicable to measuring the energy content of other types of hydrocarbon gas mixtures which include one or more diluent gases.

The energy content of a hydrocarbon mixture may be inferred by the mixture dielectric properties. The gas mixture dielectric constant is related to the mixture density by the well known Clausius-Mossotti equation and the hydrocarbon mixture density is directly relatable to the mixture gross heating value.

One practicable complication involves the effects of diluent gases ($N_2$, $CO_2$) as these gases alter the well-behaved dielectric energy content relationships developed for hydrocarbon mixtures.

The present invention is directed to a method and apparatus for measuring the dielectric constant of a gas and utilizes a column separator which is used to determine the concentration of the diluent gases. Thus, the measurement of the energy content of the gas can be corrected for diluent gas effects.

Figure 1:
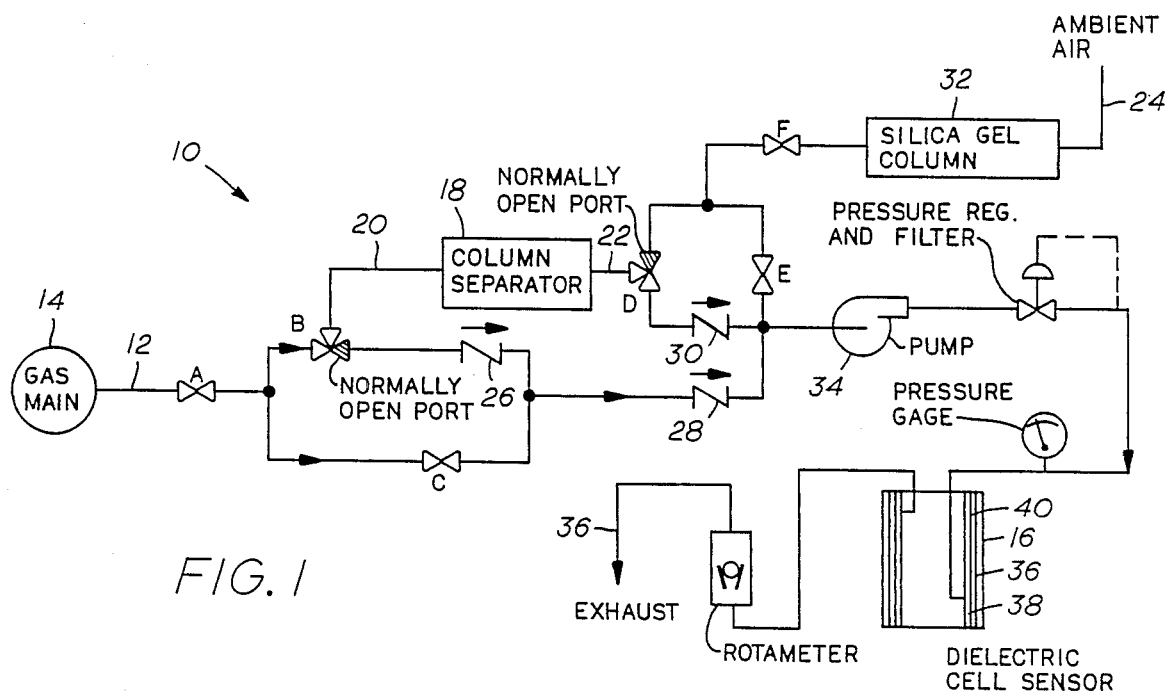
FIG. 1 is a schematic of the gas flow of the present invention.

Referring now to the drawings, and particularly to FIG. 1, the gas flow diagram of the present energy meter is generally indicated by the reference numeral 10 and generally includes a hydrocarbon gas inlet line 12 which may be connected to any suitable hydrocarbon gas mixture source such as a gas main 14, a dielectric measuring cell 16 which is connected to the gas inlet line 12 and adapted to receive a gas for measuring its dielectric constant, and a column separator 18 having an inlet 20 connected to the inlet line 12 and an outlet 22 connected to the dielectric measuring cell 16, and a purge gas line 24 connected to the column separator 18 and the dielectric cell 16.

Generally, a natural gas containing a diluent gas, such as nitrogen, enters the inlet 12 and flows through the energy meter 10 to the dielectric cell 16 thereby measuring the dielectric constant of the combination of the natural gas mixture and nitrogen. Thereafter, the gas in the inlet line 12 is passed through the column separator 18 to aid in the determination of the nitrogen which is a predominant dilute gas within natural gas. The function of the column separator 18 is to extract a binary mixture of methane and nitrogen from the multicomponent natural gas mixture in the inlet line 12. The composition of the binary gas mixture is related to the composition of the methane and nitrogen in the natural gas at the inlet 22. Thereafter this binary stream from the outlet 22 of the column separator 18 is directed through the dielectric cell 16 and its dielectric constant measured. The two measurements of the dielectric constant of the natural gas mixture and the binary mixture are then used to calculate the energy content of the natural gas and compensate for the dilute gas nitrogen in the natural gas. Thereafter a purging gas 24 is introduced into the meter 10 to purge the residual gases out of the column separator 18 and the dielectric cell sensor 16.

Valves are provided for sequentially controlling the flow of the natural gas mixture at the gas inlet 12 and the purge gas at the purge gas line 24. Thus, valves A, B, C, D, E and F are provided along with one-way check valves 26, 28, and 30. Valves A, C, E and F are conventional two-way valves and valves B and D are three-way valves. Generally, the first step of the method of operation of the meter 10 is to send a purge gas, such as ambient air, from the line 24 through a silica gel column 32 for drying the air, and thereafter through the column 18 and cell 16 in series. Thus air flows from the column 32 through valve F which is actuated to the open position, through normally opened valve D, through the separator 18, through the normally opened valve B, through check valves 26 and 28, through a pump 34 and through the dielectric cell sensor 16 to the exhaust 36 for purging the column separator 18 and dielectric cell 16. The second step of the purging includes sending purge air from inlet 24 through the silica gel 32, opening valves F and E and closing valve D for puring the cell 16, and bypassng the column 18, which also allows the cell 16 to take a dielectric air measurement reading for reference purposes. In the third step of operation, the natural gas in the inlet line 12 is passed through the dielectric measuring cell 16 in which valves A and C are opened. In the fourth step of the operation, the natural gas 12 is passed through the column separator 18 and to the dielectric cell 16 by opening valves A, B and D, while valves C, E and F remain closed.

Various types of column packing materials may be used in the column separator 18 such as activates charcoal, silica gel and a polymeric packing compound sold under the name Chromosorb 102. However, it was found that activated charcoal was the most satisfactory as in addition to extracting a binary mixture of methane and nitrogen from the multicomponent natural gas mixture, the activated charcoal would elute a tertiary mixture of nitrogen, methan and carbon dioxide from the separator 18 after the binary mixture elution. Knowledge of the binary mixture composition of nitrogen and methane could then be used to estimate the concentration of carbon dioxide in the natural gas at the inlet 12. The activated charcoal was able to transform the multicomponent natural gas stream into a binary mixture of nitrogen and methane for a reasonably long period of time before the third component, which was carbon dioxide broke through the separator to provide the tertiary mixture of nitrogen, methane and carbon dioxide for a stable tertiary time period.

While any suitable dielectric cell sensor may be used, the particular sensor 16 which was found to be satisfactory is a coaxial capacitor machined from stainless steel. The cell 16 was 12 inches long and consists of two cylinders 36 and 38 having a gap therebetween of approximately 0.025 inches and the diameter of the inner surface of the outer cylinder 36 was six inches. The measured value of the capacitance of the dielectric cell 16 was 2275 pfd.

The theory of measurement of the present meter 10 uses the well known AGA 5 equation which forms the basis for developing an energy content formula. Shown below is a simplified form of this equation that includes the effect of the diluent gas, $N_2$.

$$Ev = 1571.5 SGmix + 144 - 16.639[\%N_2] \qquad (1)$$

Clearly, the two parameters that must be determined to obtain the energy content are the specific gravity of the bulk natural gas mixture, SGmix, and the concentration of nitrogen, $\%N_2$ (in percent by volume). In the following text, the mathematical relationship between these key parameters and gas dielectric will be developed to illustrate how the energy meter 10 is capable of determining the energy content of a natural gas mixture.

Figure 2:
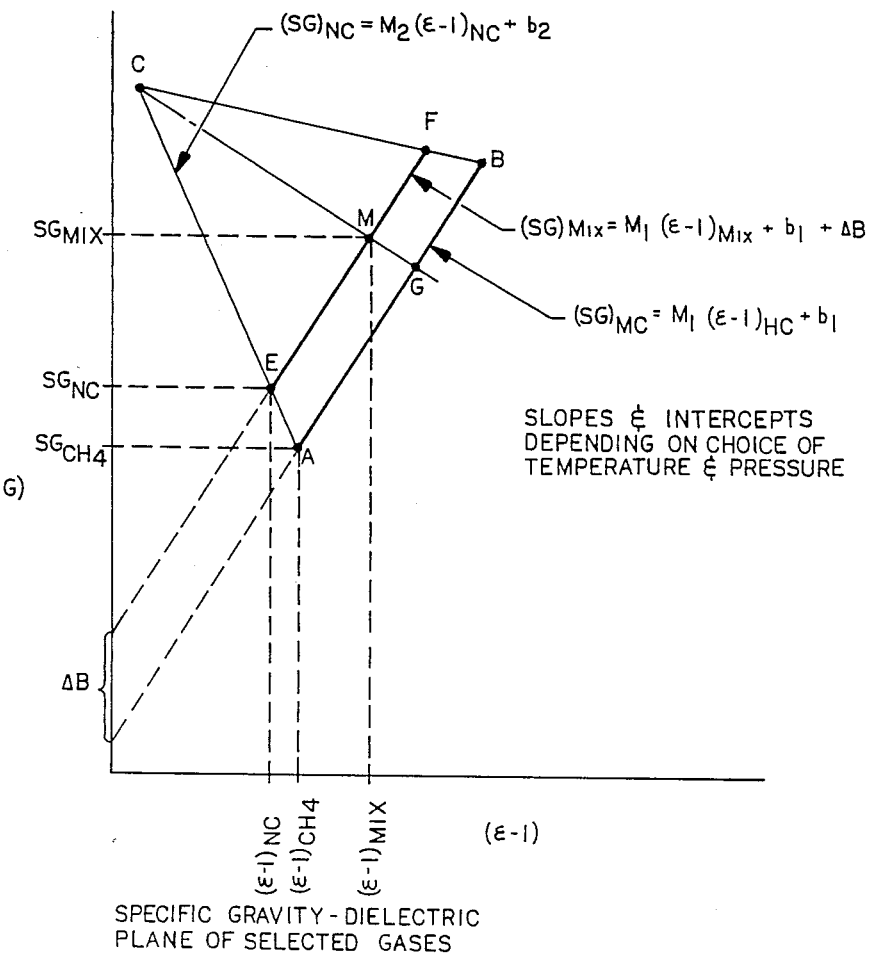
FIG. 2 is a diagram of specific gravity versus dielectric of selected gases illustrating the theory of measurement of the present invention.

Consider the triangular diagram shown in FIG. 2 which is on a graph of specific gravity versus dielectric. The apexes of the triangle represent the three major components in typical natural gas mixtures. Point A represents 100% $CH_4$, Point C represent 100% $N_2$ and Point B represents a selected pure hydrocarbon mixture containing primarily methane and other heavier hydrocarbon components. Any mixture of two of these three end points will lie on the line joined by the two end point components. For example, Line AC represents the specific gravity relationship to gas dielectric for binary mixtures containing $N_2$ and $CH_4$. The location of a binary mixture on the line determines the concentration of each component. In FIG. 2, the concentration of $N_2$ within $CH_4$ is the ratio of the length of the Line Segments AE to AC.

The locus of points for pure hydrocarbon gas mixtures fall on a line represented by Line Segment AB. In theory, the line extends without bound on the B end and it originates with the simpliest hydrocarbon gas $CH_4$, at A. Point B has been arbitrarily selected to represent a maximum SC and $\epsilon - 1$ that would exist for typical high methane hydrocarbon mixtures typical of natural gas. The line AB can be directly scaled for energy content since linear relationship exist for specific gravity versus $\epsilon - 1$ and specific gravity versus energy content for pure hydrocarbon mixtures.

A true natural gas mixture, however, will normally not fall on any one of the sides of the triangle. Rather, it will be located by a point within the triangle such as Point M, which has been arbitrarily chosen to be a line EF. This line segment represents the specific gravity to dielectric relation of a mixture containing any of the hydrocarbon mixtures denoted by Line AB with a fixed concentration of $N_2$. If the hydrocarbon mixture in question was that designated by Point B, then Point F would represent the mixture that results from the combination of Point B gas and the fixed $N_2$ concentration AE/AC. Similarly Point E would represent the specific gravity and $\epsilon - 1$ for the binary mixture of the same $N_2$ concentration and $CH_4$. For low $N_2$ concentration (i.e. <10%), Point E approximates the composition of the separated binary mixture that has been shown to elute momentarily from the column separator that is incorporated in the energy meter.

From this discussion, consider that Point M represents a typical natural gas mixture that will be analyzed on the energy meter. The task at hand is to come up with the equation to calculate SGmix and %$N_2$. From the diagram, the equation that describes line EF will yield the SGmix. To arrive at this equation, one need only to evaluate the equation of the "hydrocarbon only" gas line and adjust this by the $\Delta B$ term resulting from the Nitrogen present in Mixture M.

The constants that describe the equations in the Figure are dependent upon the temperature and pressure that is chosen for standard condition. T=74.7° F. and P=408.4 in $H_2O$ were chosen as standard. The equation of Line AB "Hydrocarbon only" line was determined from a least squares curve fit of the specific gravity and dielectric valuves for five arbitrary hydrocarbon gases shown in Table I (FIG. 3). The equation was found to be $$(SG)_{HC} = 832.1(\epsilon - 1)_{HC} - 0.1194 \quad (2)$$

In order to eavluate $\Delta B$, the equation for Line AC was also required. Another curve fit was obtained from data relating to specific gravity and dielectric for $N_2/CH_4$ mixtures shown in Table II (FIG. 4). This equation was $$(SC)_{NC} = 1552(\epsilon - 1)_{NC} = 1.81 \quad (3)$$

By using trigonometry, $\Delta B$ was determined to be $$\Delta B = 1.5366(SG)_{NC} - SG_{CH4}) \quad (4)$$

Recall that the general equation for Line Segment EF is $$SG_{mix} = M_1(\epsilon - 1)_{mix} + b + \Delta B \quad (5)$$

By substituting values for $\Delta B$ and b, and $M_1$ from equation (2), and (4), the following equation is obtained $$(SC)_{mix} = 832.1(\epsilon - 1)_{mix} - 2384.8(\epsilon - 1)_{NC} + 1.8107 \quad (7)$$

In terms of physical measurements made by the energy meter, $(\epsilon - 1)_{mix}$ is the dielectric of the bulk mixture and $(\epsilon - 1)_{NC}$ is the dielectric of the separated binary mixture eluting from the column separator.

Calculation of %$N_2$ is obtained using an equation derived from Equation (3) in which the equation was solved for concentration of $N_2$. The derived equation is shown below $$\%N_2 = 100[-3755(\epsilon - 1)_{NC} = 3.0394] \quad (7)$$

All that is necessary it to obtain the linear calibration equation relating $(\epsilon - 1)$ and $\Delta Cv$ which will be in the form of $$(\epsilon - 1) = A\Delta Cv = b \quad (8)$$

where a and b are constants determined from least square curve fit of the meter response (in a bulk gas measurement mode) to two or more known calibration gas samples. Consequently, Ev and %$N_2$ can be reduced to a function of cell 16 voltage $\Delta Cv$.

Referring now to FIG. 5, the electrical schematic of the energy measuring meter 10 is best seen which will provide a fully automatic operation. Since the capacitance change of the dielectric cell 16 is quite small, the measurement sensitivity is important. One method of measuring the capacitance of the dielectric cell 16 is an oscillator circuit, but it did not provide the required sensitivity. Accurate measurement of the capacitance was obtaind by using an AC bridge amplifier 50 such as a Validyne Engineering CD-90 in which one leg of the bridge consists of the dielectric cell 16 in series with a 2200 pfd matching capacitor and the other leg of the bridge consists of two series connected, one kilo ohm resistors. In order to compensate for variations in temperature and pressure in the dielectric cell 16, from the selected conditions of 74.7° and 408.4 inches of water, a temperature sensor 52 measures the temperature such as by Analog Devices AD590 solid state probe and a pressure transducer supplied by Sensotec is provided.

The automated control system uses a Motorola MC6802 processor 56 and the program using the above derived formula is placed in an MCM2532 EPROM58. The temperature measurement from the temperature transducer 52, the pressure measurement from the pressure transducer 54 and the cell voltage from the dielectric cell 62 are multiplexed into an ICL7109 A/D converter 60. The cell voltage is sampled by the microprocessor 56 at suitable intervals and when two successive voltage readings differ by less than 0.02 volts the voltage sample is stored. The microprocessor 56 controls solenoid drivers 60 which control the actuation of the valves A, B, C, D, E and F. The voltage from the measuring cell 16 is corrected to standard conditions from the temperature and pressure conditions that exist within the cell 16 when the cell voltage was accepted. These corrected values are then used in the derived formula to compute the Btu content of the gas which are displayed in display 62. The energy meter 10 also includes a standard RS-232 communications port 64. Cell voltage is displayed upon CRT66 at regular intervals. The CRT66 also includes a terminal for accessing a change in calibration factors.

The microprocessor actuated meter 10 starts step one of the measurement cycle by activating the solenoid driver 60 to in turn actuate the necessary valves to send purge air through both the column 16 and the dielectric cell 16. In step two, the purge air is sent directly to the dielectric cell 16 bypassing the column 18. Periodic measurements are made of the cell voltage, the temperature and the pressure. In the third step the dielectric measurement of the bulk gas mixture is performed and in the last step the dielectric of the separated binary mixture is performed. In the third step the bulk gas flow is directed straight to the capacitance cell 16 and bypasses the column 18. In the last measurement step, the bulk gas mixture flow is switched to the column separator 18 and then onto the dielectric cell 16.

It is also to be noted that in the purging cycle, in order to complete the measurement, zero reference voltages of high purity air are obtained from the measurement cell 16. After completion of a cycle, the cycle may be repeated for additional energy measurements.

The method of the present invention is readily apparent from the foregoing description of the structure and operation of the energy meter 10. However, the method includes determining the energy content of a hydrocarbon gas mixture having a diluent gas and includes the dielectric of the combination of the hydrocarbon gas mixture and diluent gas, passing the combination of the hydrocarbon gas mixture and diluent gas through a separation column for extracting a mixture containing the diluent gas, measuring the dielectric of the extracted mixture, and determining the energy content of the hydrocarbon gas mixture and diluent gas from the dielectric measurements.

The present energy meter 10 successfully demonstrated the capability of inferring the energy content of natural gas mixtures accurately to within 2.5%. The meter utilized the concept of indirect energy measurements based upon the relationship between natural gas, specific gravity and gas dielectric coupled with the ability to compensate for the dominant dilute gas in natural gas, nitrogen. The present meter provided for the accurate estimation of the concentration of nitrogen in multicomponent natural gas mixtures by using a gas separation method. The method utilized a packed column of activated charcoal to transform the multicomponent mixtures into simple binary mixtures of methane and nitrogen requiring only a simple low cost detection device for quantification.

Activated charcoal was also shown to produce a further tertiary stream containing methane, nitrogen and carbon dioxide. Once the binary mixture concentration is known, theoretically the concentration of carbon dioxide can be determined from dielectric measurements made in the tertiary mixture. However, the prototype of the instrument 10 did not perform this operation because the dielectric cell was not sensitive enough to changes in the dielectric between the binary and tertiary streams unless the concentration of carbon dioxide was greater than 1.5-2% by volume.

The present invention, therefore, is well adapted to carry out the objects and attain the ends and advantages mentioned as well as others inherent therein. While a presently preferred embodiment of the invention has been given for the purpose of disclosure, numerous changes in the details of construction, arrangement of parts, and steps of the method will be readily apparent to those skilled in the art and which are encompassed within the spirit of the invention and the scope of the appended claims.

What is claimed is:

1. A method of determining the energy content of a hydrocarbon gas mixture having a diluent gas comprising, measuring the dielectric of the combination of the hydrocarbon gas mixture and diluent gas, passing the combination of the hydrocarbon gas mixture and diluent gas through a separation column for extracting a mixture containing the diluent gas, measuring the dielectric of the extracted mixture, and determining the energy content of the hydrocarbon gas mixture and diluent gas from the dielectric measurements.

2. The method of claim 1 wherein the dielectric is measured by a dielectric cell and including, purging the separation column and the dielectric cell by air prior to the steps of claim 1.

3. The method of claim 2 wherein the separation column and dielectric cell are first purged in series and thereafter the dielectric cell is separately purged while making a dielectric measurement for reference.

4. A method of determining the energy content of a hydrocarbon gas mixture having a first and second diluent gas comprising, measuring the dielectric of the combination of the hydrocarbon gas mixture including the first and second diluent gases, passing the combination of the hydrocarbon and first and second diluent gases through a separation column for extracting a first mixture containing the first diluent gas and thereafter a second mixture containing the first and second diluent gases, measuring the dielectric of the first mixture, and thereafter measuring the dielectric of the second mixture, and determining the energy content of the hydrocarbon mixture including the first and second diluent gases from the dielectric measurements.

5. An apparatus for determining the energy content of hydrocarbon gas mixtures having a diluent gas comprising, a hydrocarbon gas inlet line for receiving a hydrocarbon gas mixture, a dielectric measuring cell connected to the gas inlet line, a column separator having an inlet connected to the gas inlet line and an outlet connected to the dielectric measuring cell, a purge gas line connected to the column separator and to the dielectric cell, valve means connected to the gas hydrocarbon inlet line, separator, measuriang cell and purge gas line for sequentially controlling the flow of a hydrocarbon gas mixture at the hydrocarbon gas inlet and purge gas at the purge gas line for purging the separator and dielectric cell with purge gas, measuring the dielectric of the gas in the hydrocarbon gas inlet, and measuring the dielectric of the gas from the outlet of the column separator, and means connected to the dielectric cell for receiving the dielectric measurements and calculating the energy content of the hydrocarbon gas mixture.

6. The apparatus of claim 5 wherein the separator includes activated charcoal.

7. The apparatus of claim 5 wherein the dielectric cell is connected to a bridge amplifier and bridge circuit.

8. The apparatus of claim 5 including temperature and gas pressure measuring means connected to the dielectric cell.

9. The apparatus of claim 5 wherein the dielectric cell includes two coaxial spaced apart metal cylinders forming a capacitor.

* * * * *

UNITED STATES PATENT OFFICE
CERTIFICATE OF CORRECTION

Patent No. 4,845,976          Dated July 11, 1989

Inventor(s) James E. Johnson et al.

It is certified that error appears in the above-identified patent and that said Letters Patent is hereby corrected as shown below:

Column 3, line 35, change "22" first occurrence to --12--

Column 3, line 65, change "puring" to -- purging --

Column 3, line 65, change "bypassng" to -- bypassing --

Column 5, line 49, change "eavluate" to -- evaluate --

Column 5, line 67, change "(7)" to -- (6) --

Column 6, line 31, change "obtaind" to -- obtained --

Column 8, line 47, change "measuriang" to -- measuring --

Signed and Sealed this

Twenty-second Day of May, 1990

Attest:

HARRY F. MANBECK, JR.

*Attesting Officer*          *Commissioner of Patents and Trademarks*